United States Patent [19]
DeToro

[11] Patent Number: 5,593,383
[45] Date of Patent: Jan. 14, 1997

[54] SECURING APPARATUS FOR AN ANKLE AND FOOT ORTHOSIS

[76] Inventor: William DeToro, 930 Trailwood Dr., Boardman, Ohio 44512

[21] Appl. No.: 407,112

[22] Filed: Mar. 20, 1995

[51] Int. Cl.$^6$ ........................................ A61F 5/00
[52] U.S. Cl. .................... 602/27; 602/23; 602/66
[58] Field of Search ...................... 602/23, 27–29, 602/66; 128/882; 36/7.5, 7.6, 7.7, 7.1 R, 110

[56] References Cited

U.S. PATENT DOCUMENTS

| | | | |
|---|---|---|---|
| 1,616,790 | 2/1927 | Fish | 36/7.7 |
| 2,207,091 | 7/1940 | Fetterling et al. | 36/7.5 |
| 2,484,935 | 10/1949 | Rooy | 36/7.7 |
| 2,628,437 | 2/1953 | Forsythe | 36/7.7 |
| 2,658,289 | 11/1953 | Schrieber | 36/7.7 X |
| 2,746,174 | 5/1956 | Patterson, Jr. et al. | 36/7.7 |
| 3,976,059 | 8/1976 | Lonardo . | |
| 5,088,479 | 2/1992 | DeToro . | |
| 5,230,681 | 7/1993 | Hannum et al. | 602/27 X |
| 5,329,705 | 7/1994 | Grim et al. | 36/110 X |
| 5,372,576 | 12/1994 | Hicks | 602/27 |
| 5,469,644 | 11/1995 | Vidler | 36/7.7 X |
| 5,486,157 | 1/1996 | DiBenedetto | 602/28 X |

*Primary Examiner*—Linda C. Dvorak
*Attorney, Agent, or Firm*—Harpman & Harpman

[57] ABSTRACT

A securing apparatus for an ankle and foot orthotic brace. The brace is used for supporting and selective immobilization of a patient's ankle and foot. The brace has a multiple part L-shaped construction with a contoured leg support portion and a foot portion having a resilient interconnecting heel portion connected therebetween. The securing apparatus includes a foot pad with aperture tabs extending therefrom and being part of the foot portion. A fabric foot engagement enclosure is provided which secures to the foot pad by a plurality of adjustable fastening straps engaged through said apertures to the aperture tabs.

9 Claims, 3 Drawing Sheets

SECURING APPARATUS FOR AN ANKLE AND FOOT ORTHOSIS

FIELD OF THE INVENTION

The present invention relates to a therapeutic leg and foot brace, and more particularly to a securing apparatus having a foot pad and fabric foot engagement enclosure for releasably securing the brace to the foot and ankle of the patient and to maintain consistent pressure against the foot, sole and ankle of the patient for therapeutic purposes.

BACKGROUND OF THE INVENTION

An orthotic foot and ankle brace typically has an L-shaped construction with a contoured leg support portion, a foot portion and a interconnecting heel portion connected therebetween. An integral fabric foot engagement enclosure is provided to secure the brace to the patient's foot and ankle. Currently, the fabric foot engagement enclosure is a one-piece integral construction which restricts air from circulating around the patient's foot. Also, the foot engagement enclosure includes an attachment portion using a pocket or sleeve, as that taught by Lonardo, U.S. Pat. No. 3,976,059 and DeToro, U.S. Pat. No. 5,088,479, which slides around and fits under and over the foot portion of the brace.

In recent times, costs for orthotic and prosthetic supplies and equipment have escalated. Therefore, the orthotic and prosthetic industry is trying to reduce costs by reusing equipment, parts and supplies when appropriate without jeopardizing a patient's health and well being. Typically a professional, usually an orthotist, would be needed to change the foot engagement enclosure of the orthotic foot brace because of contamination, or the brace would be removed and a new one applied. To change the foot engagement enclosure for the current design, the orthotist must remove screws and/or other accessories, such as the toe extension bar and walking pad to get access to the enclosure sleeve or pocket which is then slid off the foot portion.

Another problem with the current design is that it allows some lateral movement of the patient's foot since the current design does not permit uniform restraint along the foot portion. Also, the foot portion may not have a consistent width from brace-to-brace and the attachment portion of the foot engagement enclosure may not fit securely around the foot portion, thereby allowing room for additional movement of the patient's foot. This invention consistently allows for a uniform tight fit of the foot engagement enclosure to the foot portion.

Consequently, a need exists for an improved means to secure the patients foot to the orthotic brace using a fabric foot engagement enclosure, as well as an alternative to the integral enclosure design.

OBJECTS AND ADVANTAGES

Accordingly, it is an object of the present invention to provide a securing apparatus which is of a construction that provides for easy interchangeability and replacement of the fabric foot engagement enclosure. Other objectives of the present invention is to provide a securing apparatus which can better constrain the patient's foot from lateral movement and to provide an alternative to the integral foot engagement enclosure.

Other objectives and features of the present inventing will be obvious to those of skill in the art upon contemplation of the disclosure herein in connection with the accompanying drawings. It is to be understood, however, that the drawings are designed for the purpose of illustration only and not as a definition of the limits of the instant invention, for which reference should be made to the claims appended hereto.

SUMMARY OF THE INVENTION

An orthotic foot brace generally comprises a leg portion, foot portion and interconnecting heel portion connecting therebetween. The foot portion has a walking pad and a toe extension portion. A fabric foot engagement enclosure is used to attach the foot portion to the patient's foot and ankle.

The present invention overcomes the above noted drawbacks to the current construction. This invention provides for a securing apparatus comprising a foot pad being part of the foot portion. The foot pad has apertures around its outer circumference. The foot engagement enclosure is secured to the foot pad by a plurality of attachment straps extending therefrom through said apertures. This invention allows for easy removability and replacement of the foot engagement enclosure.

The instant invention also provides an alternative to the integral fabric foot engagement enclosure. The unique construction of the foot pad in this invention allows for individual padded straps to extend from the apertures to secure the patient's foot to the brace. By using individual padded straps, as opposed to the integral foot engagement enclosure, more of the patient's foot is uncovered allowing for exposure to the air.

BRIEF DESCRIPTION OF THE DRAWINGS

In the drawings, the same reference numeral denotes the same element throughout the several views.

DETAILED DESCRIPTION OF THE PREFERRED EMBODIMENTS

Figure 1:
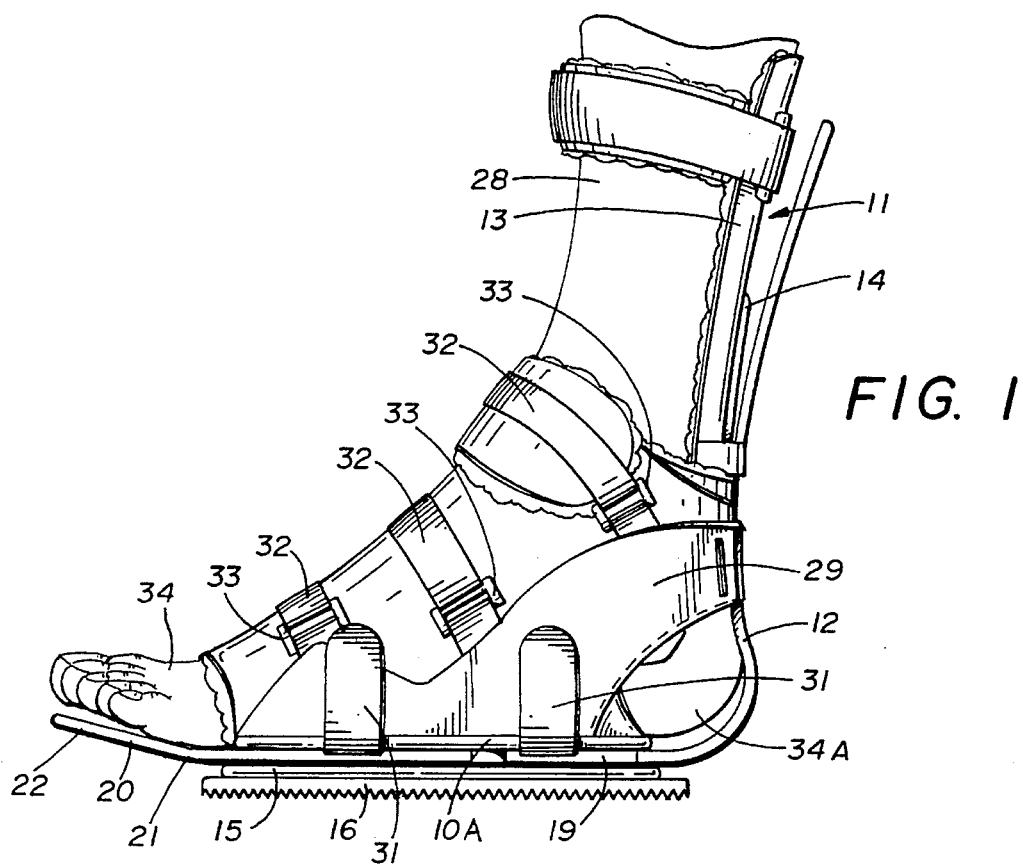
FIG. 1 is a side elevational view of the orthotic brace with securing apparatus on a patient.
Figure 2:
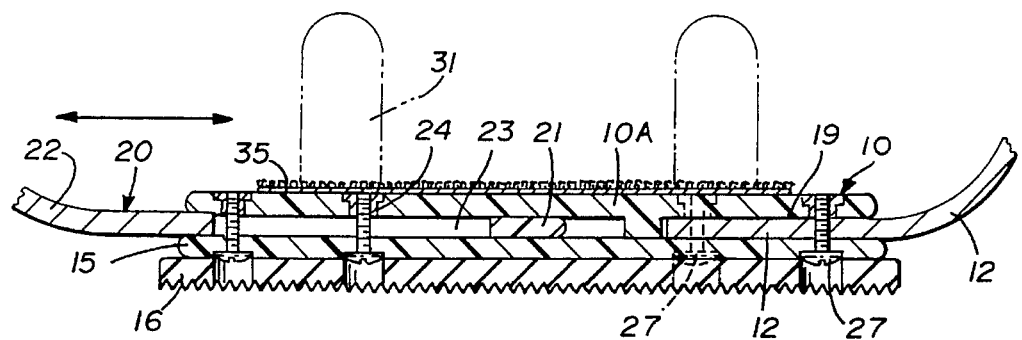
FIG. 2 is an enlarged partial cross-section of the foot portion with foot pad in the securing apparatus.
Figure 6:
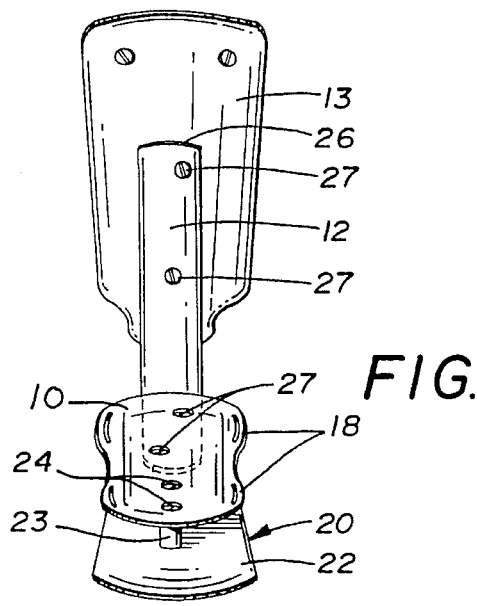
FIG. 6 is a front elevational view of an orthotic brace with the foot portion having the foot pad in the securing apparatus.

Referring to FIGS. 1, 2 and 6 of the drawings, the orthotic brace can be seen comprising a foot portion 10, a leg portion 11 and an interconnecting heel portion 12 extending therebetween. The leg portion 11 has an enlarged transversely contoured leg support 13 having a recessed channel 14 formed inwardly of one end thereof. In practice, the leg and foot portions are made of a synthetic plastic resin so that they can be molded or pre-formed into the desired contours required for engagement with a patient's leg 28 as best seen in FIG. 1 of the drawings.

The foot portion 10 has a foot pad 10A connected to a generally rectangular attachment base 15. The attachment base 15 having a resilient walking pad 16 secured thereto. The foot pad 10A is also of a generally rectangular configuration with an area of reduced transverse dimension at 17 defining pairs of longitudinally spaced apertured tabs 18. A mounting pocket 19 extends inwardly from the bottom of said foot pad 10A for engagement of the interconnecting heel portion 12 between the foot pad 10A and abutting attachment base 15.

A toe extension member 20 is adjustably secured to the foot pad 10A opposite said mounting pocket 19. The toe extension member 20 has a flat base area 21 with an upturned angularly offset end portion 22. The toe extension 20 is registerably attached between the foot pad 10A and the attachment base 15 by a mounting slot 23 aligned for registration with adjustable fasteners 24 extending from said foot pad 10A through to the attachment base 15. The slot 23 allows for the extension member 20 to move and effectively lengthen the overall foot portion 10 as indicated by the arrows in FIG. 2 of the drawings.

The interconnecting heel portion 12 is comprised of a resilient metal alloy or other suitable compound material forming a curved generally L-shaped configuration having free ends 25 and 26 which are engaged in said mounting pocket 19 in the foot pad 10A and channel 14 in the leg support portion 13, respectively. Pairs of fasteners 27 extend through the interconnecting heel portion 12 adjacent its respective ends 25 and 26 registering with selective fixed apertures in said mounting pocket 19 and leg portion 13, respectively. The effective degree of rigidity afforded the interconnecting heel portion 12 can be varied by substitution thereof with an interconnecting heel portion of greater or lesser rigidity as required to vary the overall resiliency between the leg and foot portion.

Figure 3:
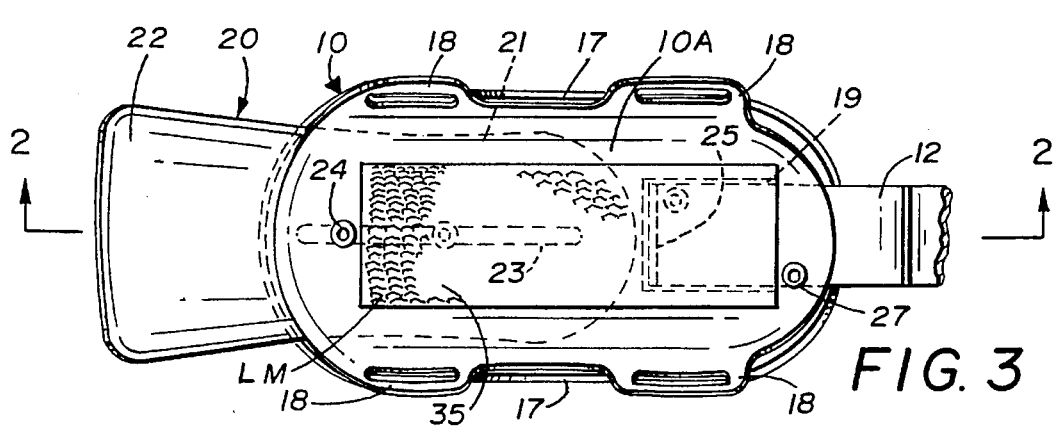
FIG. 3 is a top plan view of the foot portion with foot pad in the securing apparatus.
Figure 4:
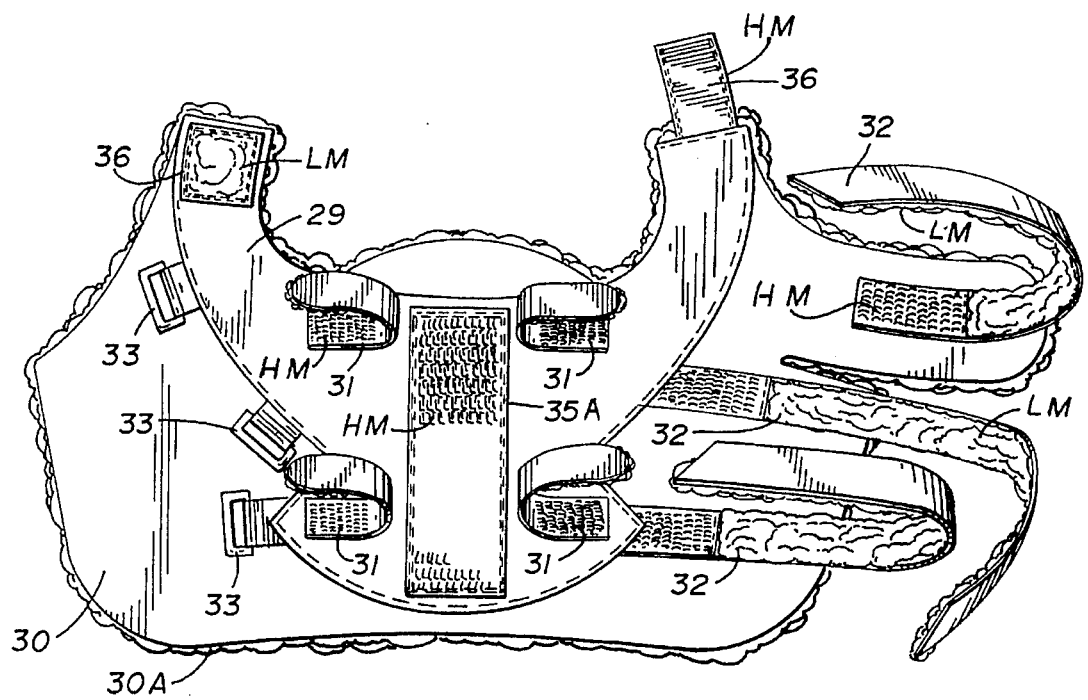
FIG. 4 is a bottom plan view of the foot engagement enclosure in the securing apparatus.
Figure 5:
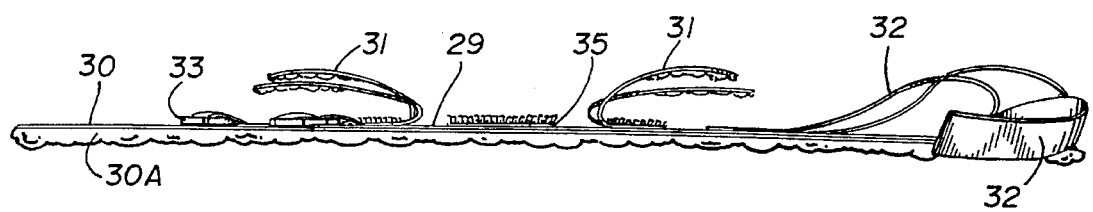
FIG. 5 is a side view of the foot engagement enclosure in the securing apparatus shown in FIG. 4.

Referring now to FIGS. 1, 4, and 5 of the drawings, a fabric foot engagement enclosure is illustrated comprising a durable mounting base portion 29 secured to a fabric sleeve 30 that is lined with a soft synthetic fur-like material 30A. The durable mounting base 29 provides a reinforced contoured mounting surface for securing multiple fastening straps 31. The fastening straps 31 are used to removably secure the foot engagement enclosure to foot pad 10A as seen in FIG. 1 of the drawings, and by viewing FIG. 3 with FIG. 4.

The fabric sleeve 30 and overlapping durable mounting base 29 define a cut out heel portion 34A as best seen in FIG. 1 of the drawings. Secondary straps 32 extend from the fabric sleeve 30 and the durable mounting base 29 for registered engagement through respective buckles 33 to secure the fabric sleeve 30 about a patient's foot 34. Releasable securing hook material HM and loop material LM, collectively referred to as releasable securing material such as VELCRO[1], is used on the fastening straps 31 and secondary straps 32 so they can be secured to themselves after engagement through respective buckles 33 and apertured tabs 18 as will be well understood by those skilled in the art.

[1] VELCRO is a registered trademark.

Turning now to FIGS. 3 and 4, it will be seen that releasable securing loop material LM is respectively positioned on the foot pad 10A at 35. The releasable securing loop material LM is aligned with releasable securing hook material HM on the durable mounting base 29 between the multiple fastening straps 31 at 35A.

It will be evident from the above description that the fastening straps 31 provide a key means for positioning and securing the foot engagement enclosure to the rigid foot pad 10A by engagement through the respective apertured tabs 18. Once the fabric sleeve 30 has been releasably secured to the foot pad 10A, it is gathered about and around the interconnecting heel portion 12 and secured by overlapping portions 36 using the same releasable securing materials LM and HM respectively, as seen in FIG. 4 of the drawings.

Thus, it will be seen that the combination of the aperture tabs 18 on the foot pad 10A with the aligned registration of the respective fastening straps 31 therethrough provide for ease of removal or adjustment of the foot engagement enclosure around the patient's foot 34.

Figure 7:
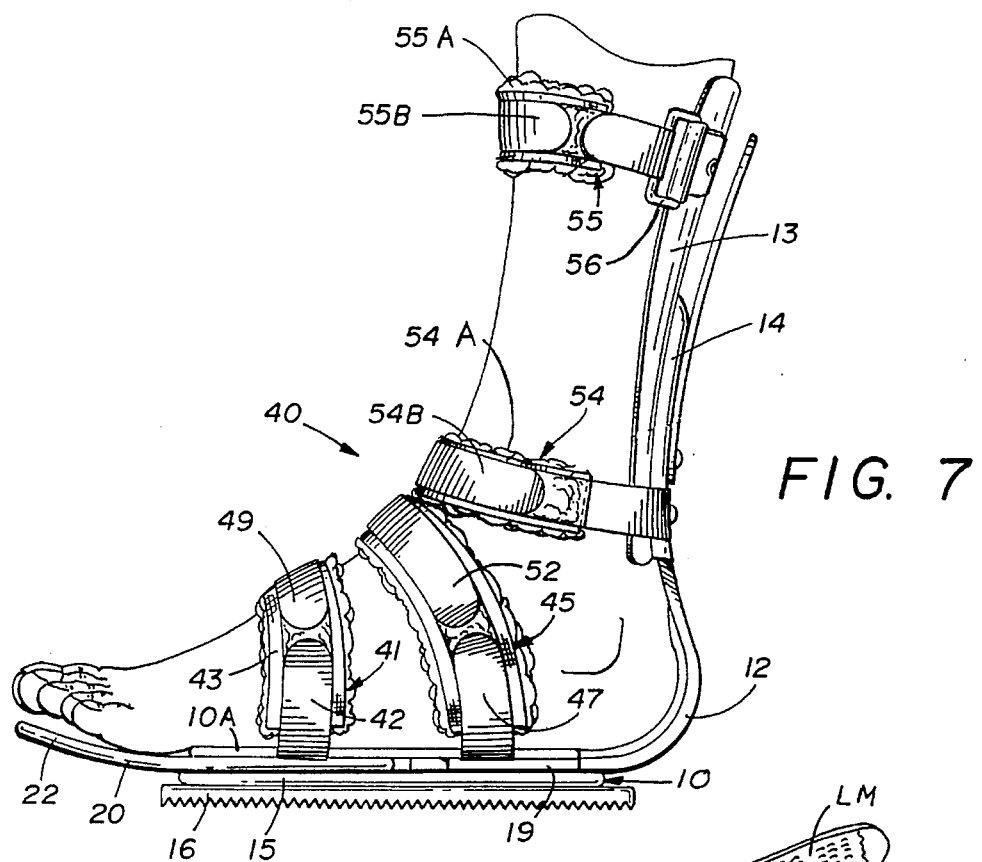
FIG. 7 is a side elevational view an orthotic brace with an alternate form of the securing apparatus.

Referring now to FIG. 7 of the drawings, an alternate form of the invention 40 is shown utilizing the hereinbefore described foot pad 10A with the aperture tabs 18, the attachment base 15 and integral resilient walking pad 16. The alternate form of the invention 40 eliminates the integral foot engagement enclosure and substitutes it with a plurality of padded strap assemblies 41, 45, 48, 51, 54 and 55 extending from respective aperture tabs 18 and said leg support 13.

Figure 8:
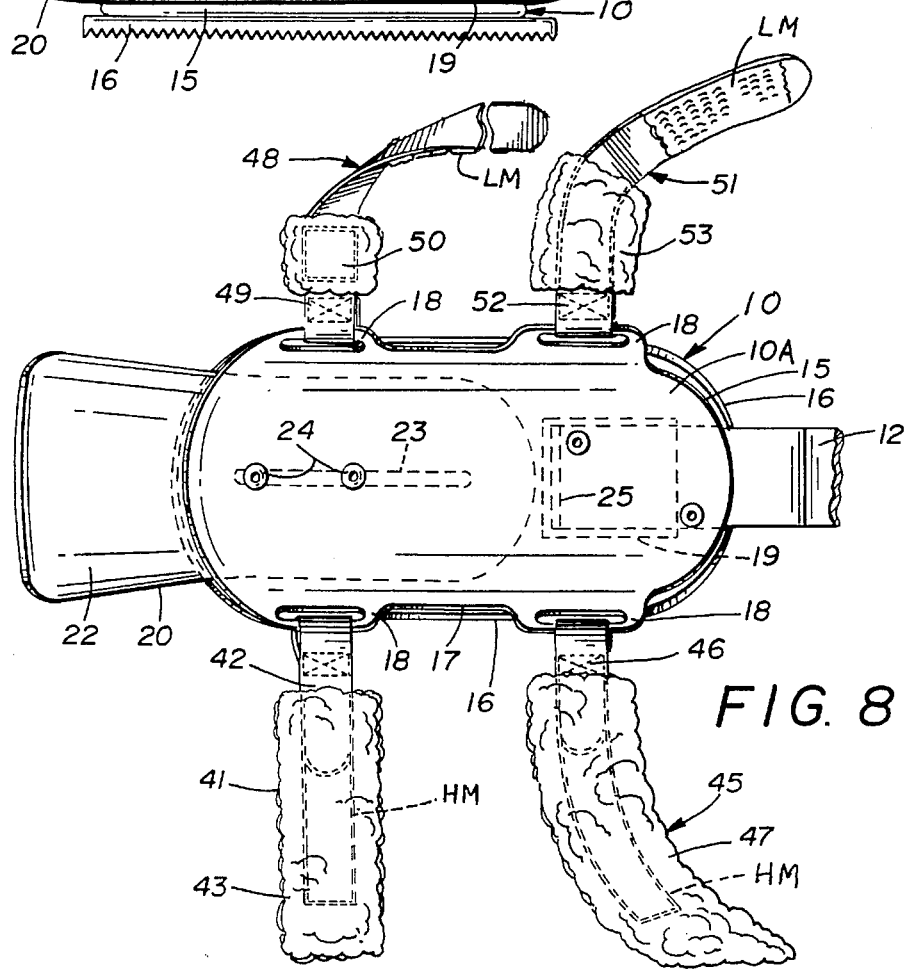
FIG. 8 is a top plan view of the alternative form of the securing apparatus with the foot removed from the illustration in FIG. 7.

Referring to FIG. 8 of the drawings, a first padded strap 41 can be seen having a strap portion 42 and fabric pad portion 43. One end of the padded strap 41 has releasable securing hook material HM and loop material LM allowing it to be extended through the aperture tab 18 and secured thereto upon itself. The opposite end of said first padded strap 41 has hook material HM thereon.

A third padded strap 48 connects to and extends from its respective aperture tab 18 using the same attachment design as described for the first padded strap 41. The third padded strap is positioned opposite said first padded strap 41, having a strap portion 49 and a padded portion 50 secured thereon. The third padded strap 48 has loop material LM positioned at the end opposite the attachment its respective aperture tab 18.

The first padded strap 41 and the third padded strap 48 extend from their respective aperture tabs 18 and pass around the patient's foot. The securing hook material HM on the first padded strap 41 secures to the loop material LM on the third padded strap 48 thereby adjustably securing the foot portion to the patient's foot.

A second strap pad 45 connects to and extends from its respective aperture tab 18 adjacent the pocket 19 in the foot pad 10A. The second padded strap 45 has a strap portion 46 and fabric pad 47 with releasable securing hook material HM and loop material LM positioned thereon as described above for said first padded strap 41 hereinbefore described.

A fourth padded strap 51 connects to and extends from its respective aperture tab 18 opposite said second padded strap 45. The fourth padded strap having a padded portion 53 attached to a strap portion 52. Like the third padded strap, the fourth padded strap 51 has loop material LM positioned at the end opposite the attachment to its respective aperture tab 18.

As described with the first padded strap 41 and the third padded strap 48 above, the second padded strap 45 and the fourth padded strap 51 extend from their respective aperture tabs 18, pass around the foot and secure to each other. The securing hook material HM on the second padded strap 45 secures to the loop material LM on the fourth padded strap 51 thereby further adjustably securing the foot portion to the patient's foot.

Referring now to FIG. 7 of the drawings, a pair of leg support straps 54 and 55 can be seen extending from said leg support 13. Each of said leg support straps 54 and 55 have a strap pad portion 54A and 55A and an adjustable strap portion 54B and 55B. The strap pad portion 55A and associated adjustable strap portion 55B are removable secured to the leg support 13 by respective buckle assemblies 56 similar to the buckles 33 as hereinbefore described.

As with the hereinbefore described padded straps 41, 45, 48 and 51, the adjustable strap portions 54B and 55B and the strap pad portions 54A and 55A extend from their respective oppositely disposed sides to overlap for adjustable releasable engagement to one another. This alternate form of the invention provides for additional flexibility of use, wherein the foot engagement enclosure described above as a preferred embodiment is not required.

While the above specification contains many specificities, these should not be construed as limitations on the scope of the instant invention, but rather as an exemplification of the preferred embodiments thereof. Accordingly, the scope of the instant invention should not be determined by the embodiments shown, but rather by the claims appended hereto and their legal equivalents.

What is claimed is:

1. Securing apparatus for a therapeutic leg and foot brace for use on a patient, said apparatus comprising:
   a) leg portion connected to a resilient interconnecting heel portion, the interconnecting heel portion being positionable behind the patient's heel and being substantially flat;
   b) a foot portion connected to the interconnecting heel portion, said foot portion having a generally flat and rigid foot pad connected to a flat walking Dad which provides stable mobility by the patient, said heel portion is attached between the foot Dad and the walking Dad, said foot pad having at least two apertured tabs formed within the outer perimeter of said foot pad, said aperture tabs being in transverse-spaced paired relation to one another;
   c) a foot engagement enclosure releasably secured to said foot pad through said apertured tabs; and
   d) means for selectively securing said foot engagement enclosure to said foot pad and to and about a patient's foot.

2. The securing apparatus of claim 1, wherein said means for selectively securing said foot engagement enclosure to said foot pad comprises a plurality of fastening straps connected to and extending from said foot engagement enclosure in registration with said respective apertured tabs.

3. The securing apparatus of claim 2, wherein said means for selectively securing said foot engagement enclosure to said foot pad further comprises having securing material on the foot pad aligned with securing material on the foot engagement enclosure between the multiple fastening straps.

4. The securing apparatus of claim 2, wherein said foot engagement enclosure further comprises:
   a) a fabric sleeve for engagement about said patient's foot, the fabric sleeve having a durable mounting base portion secured thereto;
   b) said fastening straps attached to said durable mounting base;
   c) at least two buckles attached to and extending from the outer perimeter of said durable mounting base; and
   d) at least two adjustable secondary straps being attached to and extending from the outer perimeter of said durable mounting base and being in spaced relation with said buckles for engagement therewith.

5. The securing apparatus of claim 4, wherein said fastening straps are releasably secured to said apertured tabs using hook and loop fasteners.

6. The securing apparatus of claim 5, wherein the walking pad is provided with an attachment base secured thereto.

7. The securing apparatus for a therapeutic leg and foot brace for use on a patient, the brace comprising:
   a) a foot portion interconnected to a leg portion by resilient interconnecting heel portion, the interconnecting heel portion being positionable behind the patient's heel and being substantially flat, said foot portion having a substantially flat and rigid foot pad connected to a walking pad for stable mobility by the patient, said heel portion is connected to the foot portion between the foot pad and the walking pad, said foot pad having at least one pair of apertured tabs extending along the outer perimeter of said foot pad, said aperture tabs being in transverse-spaced relation to one another;
   b) at least one pair of padded straps, each strap being attached to a corresponding aperture tab;
   c) means for adjustably securing opposing padded strap pairs to one another about a patient's foot;
   d) means for releasably securing said padded straps to the respective aperture tabs on said foot pad.

8. The securing apparatus of claim 7, wherein said aperture tabs are formed within said foot pad.

9. The securing apparatus of claim 7, wherein said means for adjustably securing the pair of padded straps to one another comprises interengaging hook and loop material on said respective strap portions.

\* \* \* \* \*